United States Patent [19]

Huber et al.

[11] Patent Number: 5,226,318
[45] Date of Patent: Jul. 13, 1993

[54] WEATHERING TESTER

[75] Inventors: James V. Huber, Oak Park; Bhakti S. Patel, Bensenville; Jacob Tikhtman, Lincolnwood, all of Ill.

[73] Assignee: Atlas Electric Devices Co., Chicago, Ill.

[21] Appl. No.: 764,154

[22] Filed: Sep. 20, 1991

[51] Int. Cl.$^5$ .......................................... G01N 17/00
[52] U.S. Cl. ........................................................ 73/159
[58] Field of Search .............. 73/159, 865.6; 313/324, 313/323, 22-24, 35, 36, 49; 62/125

[56] References Cited

U.S. PATENT DOCUMENTS

| | | | |
|---|---|---|---|
| 2,416,285 | 2/1947 | Buckingham et al. | 313/49 |
| 3,262,001 | 7/1966 | Rijckeart | 313/49 |
| 3,603,027 | 9/1971 | Degawa et al. | 313/36 |
| 3,983,742 | 10/1976 | Suga | 73/159 |
| 4,627,287 | 12/1986 | Suga . | |
| 4,704,903 | 11/1987 | Suga et al. | 73/159 |
| 4,760,748 | 8/1988 | Katayanagi et al. | 73/865.6 |
| 4,843,893 | 7/1989 | Huber et al. . | |

FOREIGN PATENT DOCUMENTS 49-32359  8/1974  Japan .
61-105444 5/1986  Japan .

*Primary Examiner*—Robert Raevis
*Attorney, Agent, or Firm*—Gerstman & Ellis, Ltd.

[57] ABSTRACT

A weathering testing system comprises a rack for carrying samples to be tested with the samples having innerfacing surfaces, and a lamp centrally positioned of the samples. Blower means are provided for directing a stream of air through the rack. By this invention, the rack may be relatively rotated with respect to the stream of air to provide added uniformity of blowing conditions to the samples. Also, the lamp may be positioned in an adjustable manner so that it can be placed parallel to the rack for optimum radiation. Also the fitting which holds the lamp may be modified so that the lamp may be installed in only a single rotational position, for increased consistency of light irradiation, which gives more uniform calibration. Likewise, an automatic technique for determining ignition and operating of the lamp is disclosed, where a current sensing system found in prior art units can be dispensed with.

17 Claims, 3 Drawing Sheets

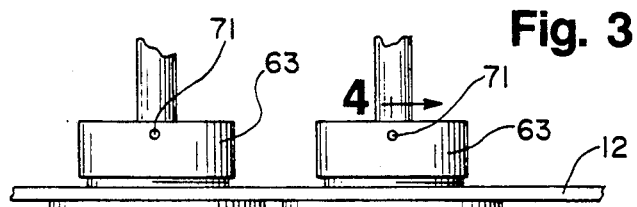
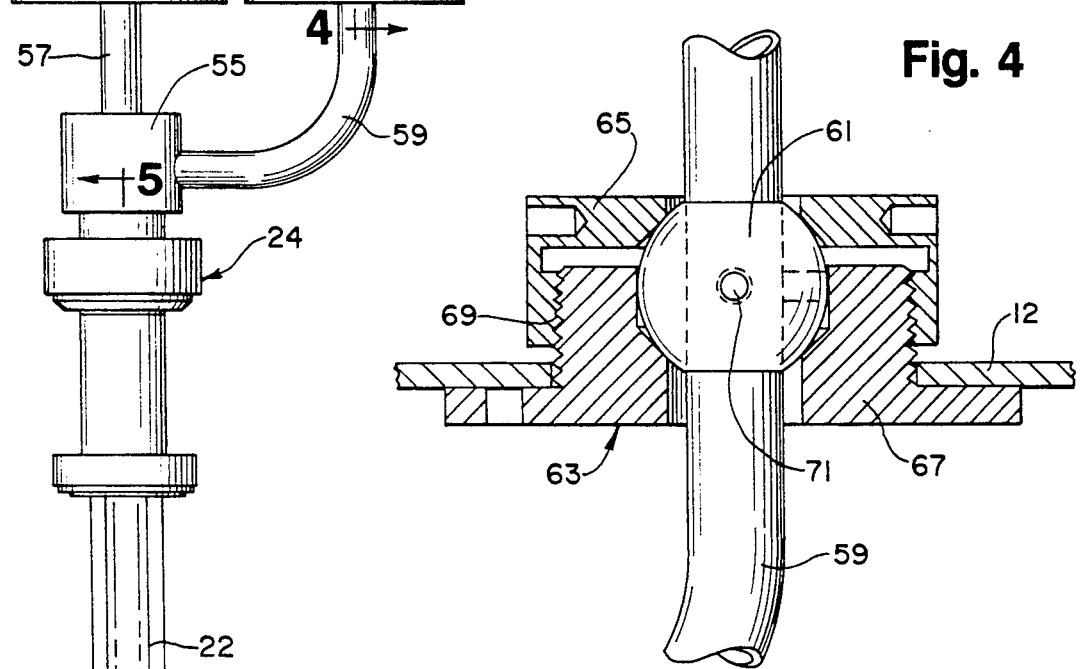
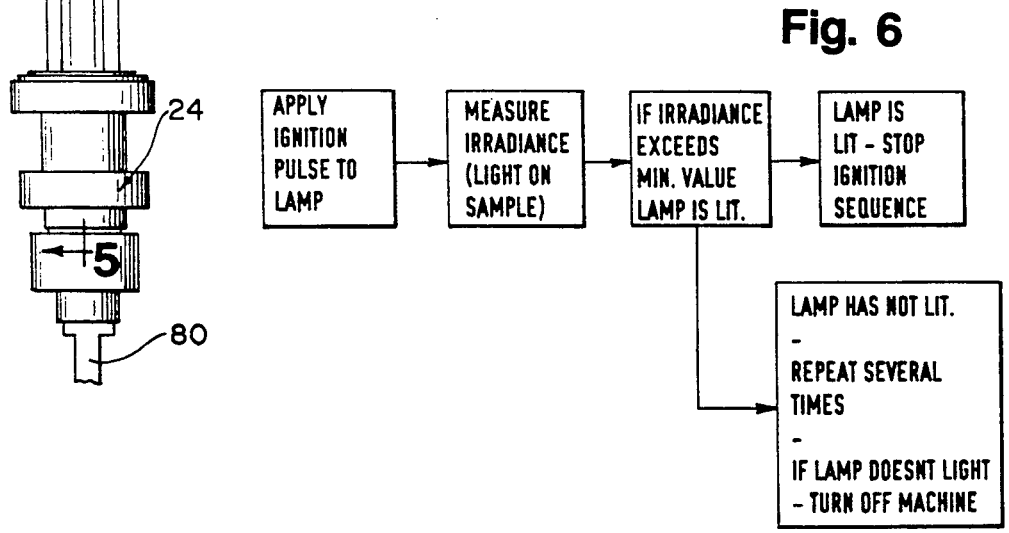

WEATHERING TESTER

BACKGROUND OF THE INVENTION

Systems for testing the weathering and lightfastness of products such as fabric samples, painted panels, and plastics are presently available, being sold for example by the Atlas Electric Devices Company of Chicago, Ill. See also Suga U.S. Pat. No. 4,627,287 and Huber et al. U.S. Pat. No. 4,843,893 for examples of such testing devices. The above devices test the weathering and lightfastness properties of materials and products under closely controlled conditions.

In the natural environment, heat, light, and moisture combine synergistically to cause optical, mechanical, and chemical changes in products which are exposed to outdoor weathering conditions. Typically, the testing apparatus of this invention and the prior art can be used to obtain such weathering data on an accelerated time basis, to permit product manufacturers to gain information as to how their products will stand up to weathering over the months or years.

As shown in the previously cited patents, a weathering testing apparatus may use air which circulates through the system to control the temperature of samples being tested so that they are not overheated by the radiation source, which typically may be a high intensity plasma lamp such as a xenon lamp. In both of the above patents, air from a pump is directed by means of a conical baffle in desired flow directions for flowing across the samples.

In accordance with this invention, improvements to weathering testing systems are provided. The samples being tested may be uniformly air cooled, with an air flow pattern which is different from, and having significant advantages over, the air flow patterns of the prior art patents cited above. Highly uniform air flow is provided, with good cooling efficiency so that a lower power air pump may operate at a lower speed of operation for savings of power, lengthening of the useful life of the air pump, and with the use of a lower capacity, lower cost pump.

Also, the high intensity plasma lamp which is used is desirably positioned in a highly uniform way so that the light emitted by the lamp remains entirely constant. However, the plasma lamp is removed from its fitting on occasion. When this is done, it is desirable for the plasma lamp to be replaced again in exactly the same rotational position as before, so that the light pattern remains constant. This is especially important when using a calibrated plasma lamp to calibrate the light monitor system.

Additionally, it is important for the high intensity plasma lamp to be precisely positioned in a central, coaxial position relative to the rack upon which the samples for testing are attached. By this invention, an adjustable fitting is provided which permits small adjustments of the plasma lamp so that it may be properly aligned and positioned.

Additionally, in the prior art, it is known to monitor the ignition of a high intensity plasma lamp in a weathering testing system by providing an electrical current flow sensing system such as an ammeter to the apparatus. By this invention, a different technique of monitoring the lighting of the lamp may be used, so that the need for the ammeter is dispensed with. In typical weathering testing apparatus, there is no need for any added hardware to replace the current flow sensing system, apart from a software program which may be installed in the microprocessor, which may be already present for other control functions.

DESCRIPTION OF THE INVENTION

By this invention, a weathering testing system is provided which comprises rack means for carrying samples to be tested. The samples have inner-facing surfaces. Means are provided for irradiating the inner-facing surfaces of the samples carried on the rack means, typically by means of a high intensity plasma lamp as described above. Blower means is also provided for directing a stream of air through the rack means.

In accordance with this invention, at least one of the rack means and the stream of air are rotatable, for the creating of uniform flow conditions. Preferably, the rack means is typically of substantially cylindrical shape. A wall is positioned adjacent one end of the substantially cylindrical rack means, positioned transversely to the axis of said rack means. An annular array of apertures is defined in the wall. The apertures are substantially positioned in the cylindrical plane which is substantially occupied by the rack means. In other words, while the annular apertures are typically slightly spaced from one end of the generally cylindrical rack, the cylindrical extension or cylindrical plane which would be defined by extending the cylindrical rack substantially intersects the apertures of the annular array.

The blower means is positioned to blow air to the side of the wall which is opposed to the rack means. Accordingly, blowing air from the blower means passes through the annular array of apertures to flow in a generally cylindrical path. Furthermore, this cylindrical path, being in the cylindrical plane of the rack means, intersects the substantially cylindrical rack means so that the air flow is in a generally cylindrical path that incorporates said substantially cylindrical rack means.

Because of this, a substantially uniform flow of air flows along the cylindrical rack, to provide uniform air flow across each of the samples for testing which are carried on the rack. This uniform flow provides new improvement in the uniformity and reproductability of results that ca be provided by the weathering testing apparatus of this invention.

Preferably specimens rotate in relation to all the air flow deflector components so that any non-uniformities due to fabrication or assembly will average out from one specimen to another.

Further in accordance with this invention, the irradiating means comprises a fitting for holding a tubular, a high intensity plasma lamp such as a xenon lamp. The fitting comprising means permitting mounting of the tubular lamp in the fitting in only a single rotational position. Thus, if the lamp is removed, when it is returned to the fitting, it will have a light intensity pattern that is constant, since it is limited to being mounted in only such a single rotational position.

The fitting and the lamp comprise pin and fitting aperture means, to cause the lamp to be mountable in only the single rotational position. Typically, the pin and fitting aperture means comprise pins and fitting apertures that extend longitudinally of the axis of the lamp.

Additionally, the fitting for holding the tubular lamp comprises at least one support rod which carries the fitting. A ball member is provided, defining an aperture through which the support rod slidingly extends. A seat is provided, carried on a frame. The seat releasably carries and rigidly retains the ball member in its normal condition.

Set screw means are provided to engage the rod into a single, desired sliding position relative to the ball member. Also, the ball member is capable of at least a degree of rotational movement from position to position in its seat, when it is released by the seat. Normally, the ball member is tightened in the seat into a single, rigid position. Thus, the longitudinal and angular position of the fitting may be adjusted so that the lamp is precisely positioned in the desired, optimum location, typically parallel to the rack.

Typically, the fitting comprises a plurality of support rods, each being associated with its own ball member, seat, and set screw means. Additionally, the seat may preferably comprise a pair of tightenable and loosenable screw-threaded members, with the ball member being positioned between the screw-threaded members so that it can be tightened therein to occupy a desired position after rotational adjustment to such a desired position.

As an additional feature of the invention, one may automatically cause ignition of a high intensity plasma lamp mounted in a weathering testing system by applying a number (typically 1 to 6) of electrical ignition pulses to the lamp across which an operating voltage is applied. The operating voltage is sufficient to cause the ignited lamp to normally operate, but generally insufficient to cause the lamp to ignite for normal operation. Thus, electrical ignition pulses of significantly higher voltage are applied to the lamp to create initial plasma-forming conditions.

One then automatically measures the irradiance emitted from the lamp after application of typically each electrical ignition pulse applied. When the measured irradiance emitted from the lamp achieves a predetermined value indicating ignition, the electrical ignition pulses are terminated, while the applied operating voltage is maintained.

The above process may be automatically applied to the apparatus by a software driven system. It has a significant advantage over the prior art ignition sensing by measurement of current flow in that, typically, a sensor for the measurement of irradiance is normally present in the weathering testing apparatus for other purposes such as calibration of the lamp. Thus, the current flow measuring means of the prior art can be eliminated, with only the need to modify the software of the apparatus so that measurement of the irradiance can be used as described above.

DESCRIPTION OF THE DRAWINGS

In the drawings.

FIG. 3 is a fragmentary, elevational view of the lamp and fitting used in the weathering testing system of FIG. 1;

FIG. 4 is a sectional view taken along line 4—4 of FIG. 3;

FIG. 6 is a flow chart showing a process for automatically igniting the lamp for operation.

DESCRIPTION OF SPECIFIC EMBODIMENTS

Figure 1:
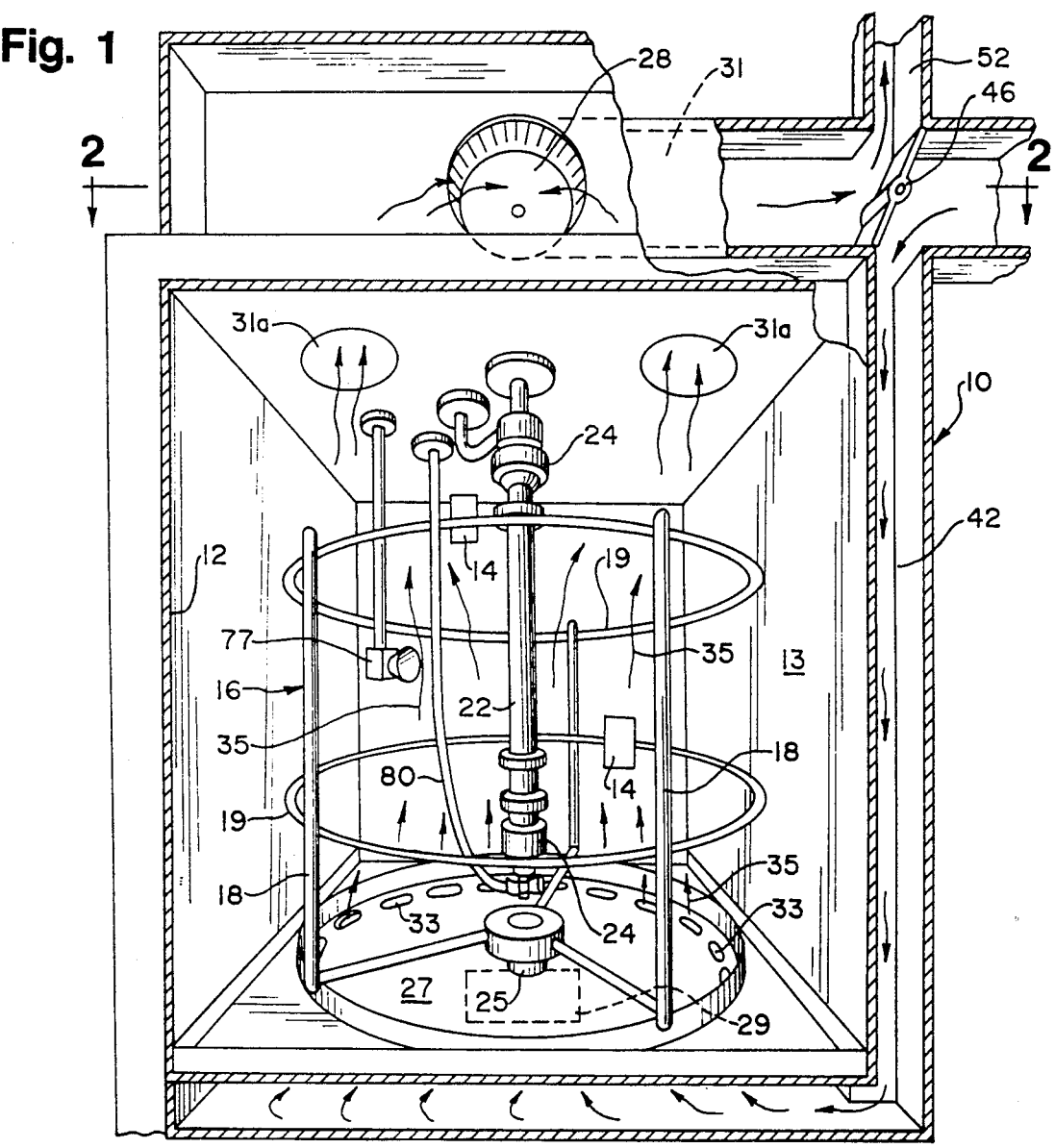
FIG. 1 is a perspective view of a weathering testing system in accordance with this invention, with portions broken away.
Figure 2:
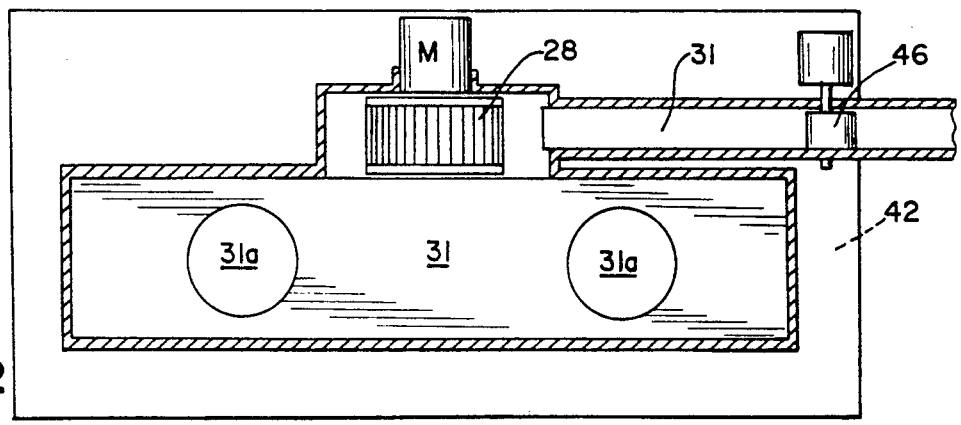
FIG. 2 is a sectional view, taken along line 2—2, of FIG. 1.

Referring to the drawings, the weathering testing system 10 of this invention comprises an outer housing 12 which defines a central chamber 13. Test samples 14 may be pieces of fabric held in a holder member, painted panels, pieces of plastic, or the like, for which weathering resistance data is desired.

Test samples 14 may be carried on a rack 16, which may be made as shown out of a generally cylindrical array of longitudinal and circumferential stainless steel struts 18, 19, to which test samples 14 may be attached.

At the center of generally cylindrically rack 16, in substantially coaxial relation therewith, a high intensity lamp 22 is positioned, being carried in a fitting 24. Specifically, the high intensity lamp 22 may be a plasma lamp such as a xenon lamp, positioned in coaxial relation with the generally cylindrical frame 16 so that all samples 14 may receive substantially uniform irradiation, being all positioned substantially perpendicular to radii extending outwardly from the essentially common axis of the lamp 22 and cylindrical rack 16 to each test sample.

Rack 16 is carried on a bottom axle 25, which extends through end wall 27 positioned adjacent an end of rack 16, which end wall is in substantially perpendicular relation to the axis of rack 16.

In accordance with this invention, electric motor 29 may be provided to cause axle 25 and the attached rack 16 to rotate relative to lamp 22 and end wall 27. Thus, by this means, the rotation of rack 16 about its axis provides increased uniformity of the radiation conditions encountered by the various samples 14 carried thereon.

Blower 28, powered by motor M, is positioned in a plenum 31 communicating between blower 28 and chamber 13 through top holes 31a.

Wall 27 defines a plurality of spaced apertures 33, the apertures being arranged in a circular array completely about the peripheral area of wall 27. The origin of the circular array of apertures 33 is positioned substantially on the common axis of rack 16 and lamp 22. Circular array of apertures 33 also has an essentially common radius to the radius of substantially cylindrical rack 16, so that apertures 33 are substantially positioned in the cylindrical plane substantially occupied by the rack 16. Thus, blowing air, passing through the circular array of apertures 33, flows in a generally cylindrical path as indicated by arrows 35, which cylindrical path incorporates the substantially cylindrical rack 16. Thus, the various samples 14 are positioned in the generally cylindrical current of air that passes along the cylindrical area of the rack, to encounter highly uniform air flow conditions. This uniformity is increased by the rotation of rack 16, so that highly reproducible results of weathering testing can be obtained with respect to the various samples 14.

As an alternative design, rack 16 may be stationary, and wall 27 may rotate so that the respective apertures 33 rotate in a circular path within the area of the circular plane occupied by generally cylindrical rack 16, to achieve similar results.

Pivoting valve member 46 defines a pair of pivoting flaps as shown. In the position of valve 46 shown, single-pass flow of air takes place through the system, with inlet air flow passing through passageway 42 to chamber 13 through apertures 33, and then to pass through apertures 31a to blower 28 and then through outlet 52. However, valve member 46 may be rotated about 45 degrees counterclockwise to close outlet aperture 52, and to connect plenum 31 with passageway 42, for recirculating flow of air. Damper 46 may also occupy any desired intermediate position to allow some fresh air inlet and some recirculation of air.

A light sensing rod 77 is provided to monitor the intensity of light emitted by lamp 22, for calibration of the system. Also, if desired, a black panel sensor may be carried on rack 16 in a position corresponding to the positions of samples for testing 14, and the system may be controlled with that and/or other sensors, for example as described in Huber et al. U.S. Pat. No. 4,843,893.

Referring to FIGS. 3 and 4, the positioning of lamp 22 and fitting 24 may be controlled by the following means.

Fitting 22 defines a block 55 from which a pair of support rods 57, 59 extend, support rod 59 bending outwardly and then into parallel relation with support rod 57.

FIG. 4 shows detailed structure of support rod 59 and its retention to the outer housing wall 12. The structure pertaining to support rod 57 is essentially identical thereto. Both rods 57, 59 are hollow tubes for conveying cooling water to and from lamp 22.

Support rod 59 extends through an aperture in a ball member 61 in sliding relation therewith. Ball member 61 is carried in a seat 63 which comprises upper seat 65 and lower seat 67 which are shown to be threadedly attached to each other through threads 69. Lower seat 67 is attached by welding, bolting, or the like, to outer housing wall 12, being shown to reside in an aperture of said housing wall. A set screw 71 extends through a threaded aperture in ball 61 to engage the support rod 59. Thus, the longitudinal, sliding position of each support rod 57, 59 can be adjusted by its respective set screw 71, by releasing the respective set screws and sliding each support rod 57, 59 until lamp 22 and fitting 24 ar positioned at the precisely desired vertical position. Simultaneously, upper seat portions 65 may be unscrewed, to loosen the gripping relation of seat 63 on ball 61, so that ball 61 can rotate to a small degree as the fitting 24 and lamp 22 are adjusted both vertically and with respect to angular orientation to the exact, desired position.

Then, the respective upper seat portions 65 are tightened by screwing so that each respective ball 61 becomes immovable; and set screws 71 are tightened to lock fitting 24 and lamp 22 into the precisely desired position.

Figure 5:
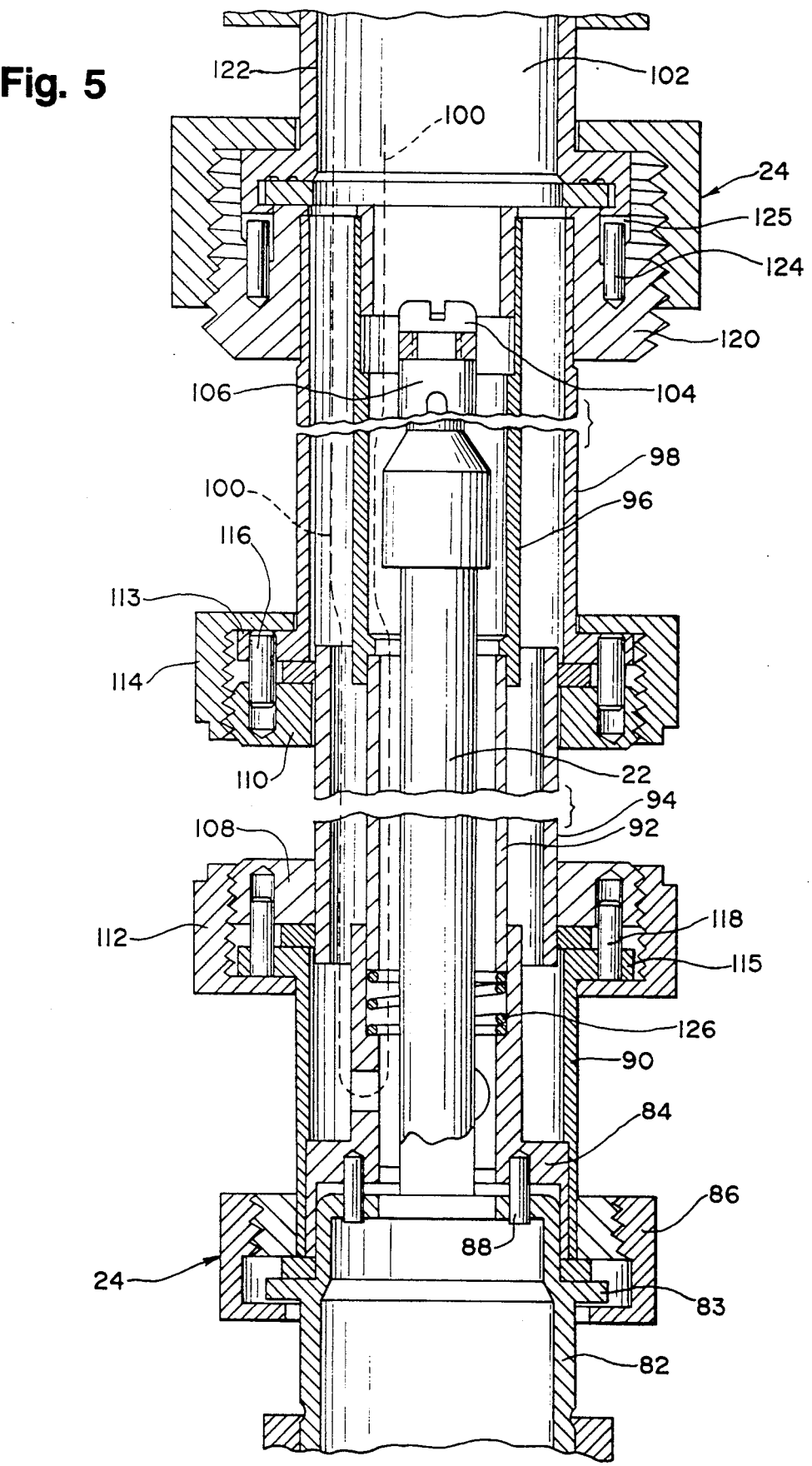
FIG. 5 is a sectional view taken along line 5—5 of FIG. 3, showing how the lamp is secured within the fitting of the apparatus of FIG. 1 with some parts removed for clarity.

Referring to FIG. 5, the tubular xenon lamp 22 and its fitting 24 are shown in detail. Electrical power is provided to the lamp system by cable 80, see FIG. 1.

Lamp 22 defines a lamp base 82 which is carried at flange 83 between inner sleeve 84 and union ring 86. Pins 88 are provided so that lamp base fits with member 84 only in a single rotational position. For example, pins 88 can fit through corresponding hole in members 82 and 84, being distributed in an asymmetrical manner so that only one fitting, rotational position is possible. Alternatively a single pin and hole may be used in each longitudinal position rather than multiple, asymmetrically placed pins. Inner tube 84 is surrounded by an outer tube 90, to define part of the cooling water flow path of the system.

Inner and outer light filter tubes 92, 94 are defined along the majority of the length of lamp 22 to provide the desired light distribution curve. Second inner and outer tubes 96, 98 are defined at the other end of lamp 22, so that a tubular water flow path as defined by arrow 100 may be provided. The water inlet and outlet lines may comprise rods 57, 59 which are hollow and tubular, and may conventionally connect with water conduits to define the flow path 100, in an appropriate manner understandable to those skilled in the art.

At the upper end of the lamp, burner socket nut 104 is provided, holding burner socket 106, which in turn, holds the upper end of lamp 22.

Inner and outer tubular light filters 92, 94 may be carried in a pair of threaded rings 108, 110 at their respective ends, which threaded rings respectively communicate with threaded union rings 112, 114. Flange 113 of outer tube 98 and threaded ring 110 each define apertures in which reside pin members 116 distributed in asymmetric manner so that the apparatus can connect only in a single rotational position. Likewise, a flange 115 of lower outer ring 90 and union ring 108 carry similar apertures so that pins 118 may be inserted, with pins 118 being asymmetrically distributed for the same reason.

At the top of the apparatus, threaded top fitting 120 is provided, with threaded ring 123 threading thereon to retain water fitting seat 122, with dowel pins 124 being provided, each fitting into slot 125 of water fitting seat 122.

Spring 126 is also provided as shown to urge inner light filter tube 92 upwardly, away from inner tube 84, to accommodate for heat expansion and for other dimensional discontinuities in the system.

Referring to FIG. 6, a flow chart for igniting lamp 22 and determining such ignition is disclosed. Lamp 22 is a conventional lamp which has conventional ignition means, by which a pulse of increased voltage is passed through the lamp, to initially ionize the gases therein.

In accordance with the process of FIG. 6, a pulse of such ignition is applied to the lamp. Then, the irradiance of the lamp is measured by irradiance sensor 77 (FIG. 1), with the signal being sent to control software of the system. If the irradiance exceeds the minimum value, the lamp is lit, and the ignition pulses terminate. However, if the lamp has not lit, typically, the software of the system will cause ignition pulses to repeat several times. If after the predetermined number of repetitions the lamp does not light as indicated by irradiance sensor 77, the software turns off the system, and a signal is activated to alert the operator to the failure.

As previously stated, this process has the significant advantage that it is not necessary to measure current flow through the lamp by means of an ammeter or the like, so the ammeter and related parts may be dispensed with.

The above has been offered for illustrative purposes only, and is not intended to limit the scope of the invention of this application, which is as defined in the claims below.

That which is claimed is:

1. In a weathering testing system which comprises: rack means for carrying samples to be tested, said samples having inner-facing surfaces, means for irradiating the inner-facing surfaces of said samples carried on said rack means, and blower means for directing a stream of air through said rack means, the improvement comprising, in combination:

a wall positioned adjacent one end of said rack means and positioned transversely to the longitudinal axis thereof; annular aperture means defined in said wall, said aperture means being substantially positioned in a cylindrical plane substantially occupied by said rack means, said blower means being positioned to blow air to the side of said wall opposed to said rack means, whereby blowing air from said blower means passes through said aperture means to flow in a generally cylindrical path that incorporates said rack means.

2. The weathering testing system of claim 1 in which said irradiating means comprises a fitting for holding a tubular lamp, said fitting comprising at least one support rod which carries said fitting; a ball member defining an aperture through which said support rod slidingly extends; a seat carried on a frame, said seat releasably carrying and rigidly retaining said ball member; set screw means to engage said rod and lock it into a single, desired sliding position, said ball member being capable of at least a degree of rotational movement from position to position in said seat when released by said seat, and to be tightened into a single, rigid positions, whereby the longitudinal and angular position of said fitting may be adjusted.

3. The weathering testing system of claim 2 in which the set screw means is carried by the ball member.

4. The weathering testing system of claim 2 in which said fitting comprises a plurality of said support rods and associated ball members, seats, and set screw means.

5. The weathering testing system of claim 2 in which said seat comprises a pair of tightenable and loosenable screw-threaded members, said ball member being positioned between said screw-threaded member.

6. The weathering testing system of claim 1 comprising means for relatively rotating said rack with respect to said wall and aperture means.

7. The weathering testing system of claim 1 in which said irradiating means comprises a fitting for holding a tubular lamp, said fitting comprising means permitting mounting of said lamp in the fitting in only a single rotational position.

8. The weathering testing system of claim 7 in which said lamp and structure defining a fitting comprise a pin and fitting aperture carried respectively on said lamp and fitting.

9. The weathering testing system of claim 8 in which said lamp defines a plurality of said pins and structure defining fitting apertures that extend substantially parallel to the axis of said lamp.

10. The weathering testing system of claim 1 in which said rack means is of substantially cylindrical shape.

11. In a weathering testing system which comprises: rack means for carrying samples to be tested, said samples having inner-facing surfaces, means for irradiating the inner-facing surfaces of said samples carried on said rack means, and a blower means for directing a stream of air through said rack means, the improvement comprising, in combination:

said irradiating means comprising a fitting for holding a tubular lamp, said fitting comprising at least one support rod which carries said fitting; a ball member defining an aperture through which said support rod slidingly extends; a seat carried on a frame, said seat releasably carrying and rigidly retaining said ball member; set screw means to engage said rod and lock it into a single, desired sliding position, said ball member being capable of at least a degree of rotational movement from position to position in said seat when released by said seat, and to be tightened into a single, rigid position, whereby the longitudinal and angular position of said fitting may be adjusted.

12. The weathering testing system of claim 11 in which the set screw means is carried by the ball member.

13. The weathering testing system of claim 11 in which said fitting comprises a plurality of said support rods and associated ball members, seats, and set screw means, said support rods comprising tubing for conveying cooling water to an from said irradiating means.

14. The weathering testing system of claim 13 in which said seats comprise a pair of tightenable and loosenable screw-threaded members, said ball member being positioned between said screw-threaded members.

15. The weathering testing system of claim 11 in which a tubular lamp is carried in said fitting, said lamp and fitting comprising means permitting mounting of said lamp in the fitting in only a single rotational position.

16. The weathering testing system of claim 15 in which said means permitting mounting of said lamp comprises pin and fitting aperture means carried respectively on said lamp and fitting.

17. In a weathering testing system which comprises: rack means for carrying samples to be tested, said samples having inner-facing surfaces, means for irradiating the inner-facing surfaces of said samples carried on said rack means, and blower means for directing a stream of air through said rack means in a direction generally parallel to the longitudinal axis of said rack means, the improvement comprising, in combination:

means for relatively rotating said rack means with respect to said stream of air about said longitudinal axis; said irradiating means comprising a fitting for holding a tubular lamp, said fitting comprising at least one support rod which carries said fitting; a ball member defining an aperture through which said support rod slidingly extends; a seat carried on a frame, said seat releasably carrying and rigidly retaining said ball member; set screw means to engage said rod and lock it into a single, desired sliding position, said ball member being capable of at least a degree of rotational movement from position to position in said seat when released by said seat, and to be tightened into a single, rigid position, whereby the longitudinal and angular positions of said fitting may be adjusted.

* * * * *